(12) United States Patent
Lee

(10) Patent No.: US 10,610,641 B2
(45) Date of Patent: Apr. 7, 2020

(54) APPARATUS AND SYSTEM FOR FLUID DELIVERY

(71) Applicant: EPIC MEDICAL PTE LTD, SG (SG)

(72) Inventor: Freddie Eng Hwee Lee, SG (SG)

(73) Assignee: Epic Medical PTE Ltd, Singapore (SG)

( * ) Notice: Subject to any disclaimer, the term of this patent is extended or adjusted under 35 U.S.C. 154(b) by 390 days.

(21) Appl. No.: 15/607,018

(22) Filed: May 26, 2017

(65) Prior Publication Data

US 2017/0340820 A1 Nov. 30, 2017

(30) Foreign Application Priority Data

May 30, 2016 (SG) .......................... 10201604323Y

(51) Int. Cl.
| | |
|---|---|
| *A61M 5/168* | (2006.01) |
| *A61M 5/142* | (2006.01) |
| *A61M 5/178* | (2006.01) |
| *A61M 5/31* | (2006.01) |
| *A61M 5/315* | (2006.01) |
| *A61M 39/28* | (2006.01) |

(52) U.S. Cl.
CPC .... *A61M 5/16881* (2013.01); *A61M 5/14244* (2013.01); *A61M 5/16804* (2013.01); *A61M 5/16831* (2013.01); *A61M 5/1782* (2013.01); *A61M 5/3129* (2013.01); *A61M 5/31505* (2013.01); *A61M 39/287* (2013.01); *A61M 2005/3131* (2013.01)

(58) Field of Classification Search
CPC .............. A61M 5/1454; A61M 5/1456; A61M 5/2033; A61M 2005/14506; A61M 5/16881; A61M 5/3129; A61M 5/31505
See application file for complete search history.

(56) References Cited

U.S. PATENT DOCUMENTS

| | | | |
|---|---|---|---|
| 4,059,110 A | 11/1977 | Wuthrich | |
| 4,755,172 A | 7/1988 | Baldwin | |

(Continued)

FOREIGN PATENT DOCUMENTS

| | | |
|---|---|---|
| EP | 0824923 A1 | 2/1998 |
| EP | 1728529 A1 | 12/2006 |

(Continued)

OTHER PUBLICATIONS

European Patent Application No. 17173314.0; Extended Search Report; dated Jan. 15, 2018; 7 pages.

*Primary Examiner* — Bradley J Osinski
(74) *Attorney, Agent, or Firm* — BakerHostetler

(57) ABSTRACT

An apparatus for delivering fluid from a fluid container comprises a housing to which a fluid container is attachable, a slider movably disposed in the housing and a resilient having a first end connected to the housing and a second end connected to the slider. Upon receiving an external force, the slider moves relative to the housing from a first position toward a second position to deform the resilient member from an original state to a deformed state, and upon release of the external force, the resilient member is allowed to resume to the original state to move the slider toward the first position to urge the slider against the fluid container to deliver fluid from the fluid container under a constant fluid flow rate.

16 Claims, 12 Drawing Sheets

(56) References Cited

U.S. PATENT DOCUMENTS

| | | | | |
|---|---|---|---|---|
| 4,863,429 A | * | 9/1989 | Baldwin | A61M 5/1454 |
| | | | | 604/135 |
| 5,800,405 A | * | 9/1998 | McPhee | A61M 5/1454 |
| | | | | 604/135 |
| 2017/0246381 A1 | * | 8/2017 | O'Neil | A61M 5/14546 |

FOREIGN PATENT DOCUMENTS

| | | |
|---|---|---|
| GB | 2534599 A | 8/2016 |
| WO | WO 2014/170267 A1 | 10/2014 |
| WO | WO 2017/080814 A1 | 5/2017 |

\* cited by examiner

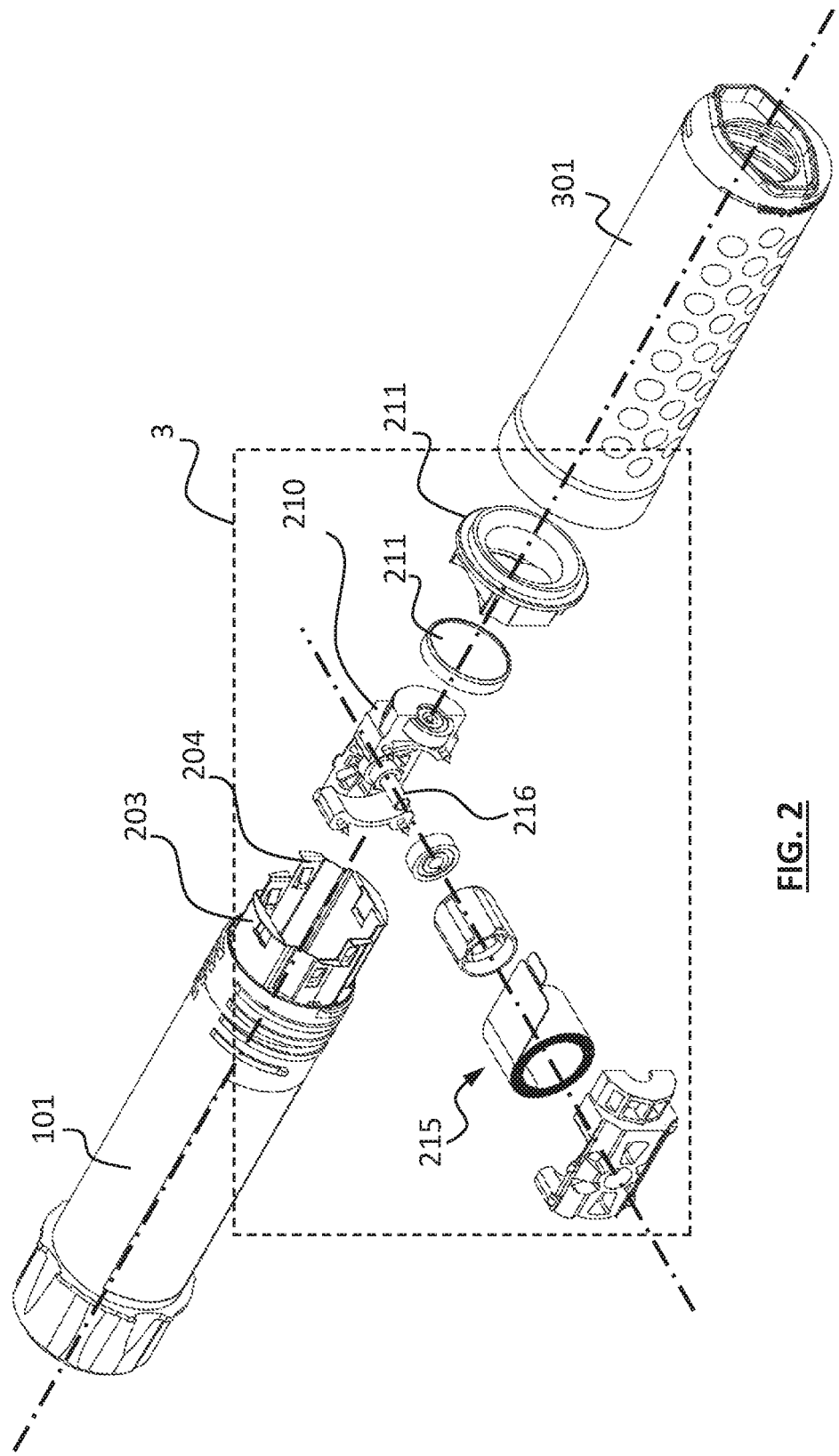

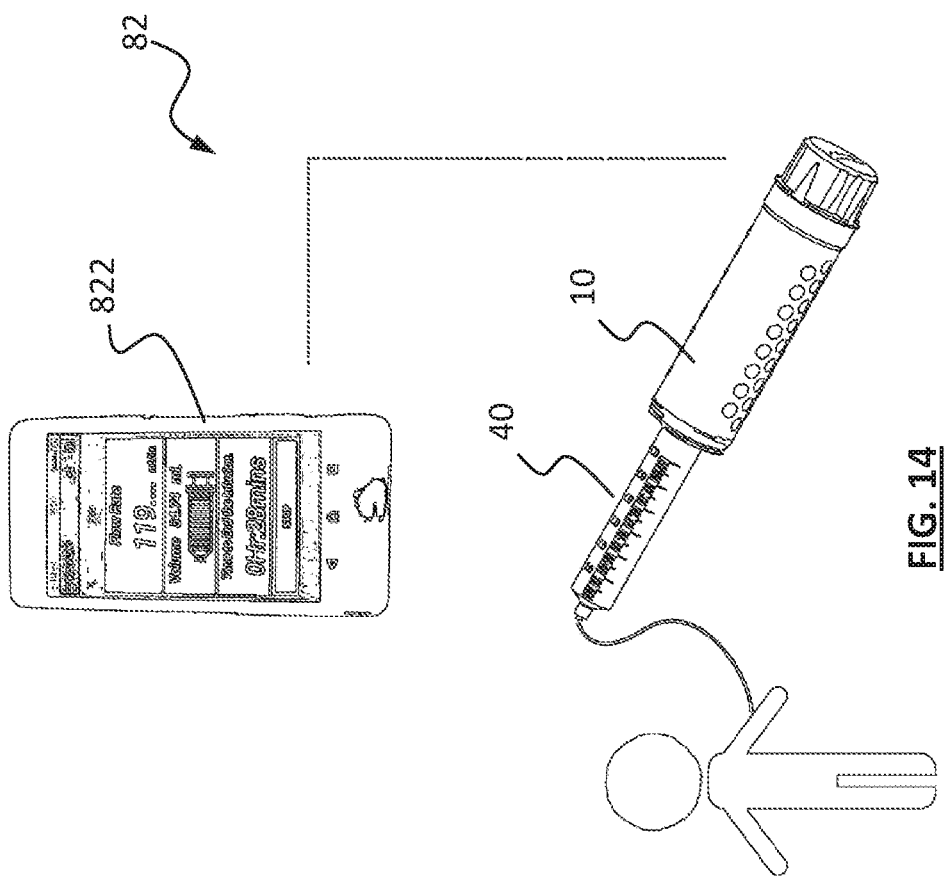

APPARATUS AND SYSTEM FOR FLUID DELIVERY

CROSS-REFERENCE TO RELATED APPLICATIONS

This claims priority to Singapore Patent Application Serial No. 10201604323Y filed May 30, 2016, the disclosure of which is hereby incorporated by reference as if set forth in its entirety herein.

TECHNICAL FIELD

The present disclosure relates to an apparatus and system for delivering fluid from a fluid container. In particular, it relates to an apparatus and system for infusion and injection of fluid medical substance.

BACKGROUND

The use of ambulatory, mechanically driven infusion devices or pumps have gain wide acceptance due to its ease of use, safe and effective means of drug delivery in both hospital and non-hospital based settings. The salient benefits are derived from the absence of programming or infusion settings, unlike electronic pumps which can lead to serious adverse events arising from human errors.

The general principle of such mechanical pumps is based on a force or pressure action on a body of fluid within an enclosed container or receptacle such that the fluid is pushed out through a flow restrictor connected to the container. For any given pressure acting on the fluid, the flow rate achieved is determined by the internal diameter of the lumen of the restrictor based on Bernoulli's and/or Hagen principle.

Albeit the safety element imbued in mechanical pumps, there are limitations that relates to flow accuracy and costs, particularly when the pump is intended for single use only. The flow rate accuracy which is typically designed to meet prevalent international standards of +/−15% limits the device to its use with only drugs that allow greater tolerant ranges. There are also other issues pertaining to storage and operational use, for example if the device is constructed with elastomeric membranes as reservoir, the pressure generated would be affected by the time duration and conditions of storage.

SUMMARY

In one embodiment, a reusable spring driven apparatus that enables fluid delivery including the infusion of medication at an accurate and uniform flow rate is disclosed.

The disclosed embodiments can employ the use of a constant force tape spring to produce a significantly uniform force that acts on a body of fluid filled in a generally tubular container such as a syringe. In one embodiment, a syringe has a rigid cylindrical barrel that is open on the back end and a plunger or a piston like contraption is axially movable within the container through the back end. The front end of the barrel has a tip or nozzle that lends itself to fluid communication with the outlet of a tube along which a flow restriction element such as a valve or a clip is provided, either by its internal diameter or a purposely designed capillary in its path. When the plunger, which includes a fluid sealing feature, is pushed towards the nozzle, the fluid contents e.g. liquid medicine inside the barrel would be discharged via the nozzle.

The apparatus that drives the plunger includes a resilient member, e.g. a constant force spring of a thin, flat tape shape connected to a slider which is movably disposed in a housing. The spring has a first end protruding out of the slider and connected to the housing, and a second end connected to the slider. When no external force is applied, the spring is coiled about the second end, with a major portion of the spring wounded and received in the slider. When an external force is applied to the slider, as the first end of the spring is connected to the housing, the slider is moved relative the housing in a direction away from the first end, to create the required linear displacement that uncoils the spring out of the slider to store a potential energy in the spring. A syringe can be attached to the housing, with the plunger abutting against the slider. The slider counteracts against the plunger to exert a driving force to the plunger. When the valve or clip connected to the nozzle of the syringe is opened, the potential energy stored in the spring is allowed to release, such that the driving force presses against the plunger in pushing the fluid out of the syringe, to deliver the fluid to a user e.g. a patient to whom the syringe is connected.

In one embodiment, an apparatus is configured to support syringes filled with any volume of liquid medicine up to the maximum capacity that is specified for a particular model of a syringe. This feature provides less limitations to the selection and use of the syringes as the volume of medication needs no longer be restricted to any specified volume of liquid medicine filled in the syringe.

In one embodiment, the housing includes a hollow mandrel in which the slider is movably disposed, and a sleeve telescopically coupled to an external side surface of the mandrel, through helical thread grooves formed on the inner surface of the sleeve and corresponding helical thread ridges formed on the external surface of the hollow mandrel. When an external force is applied against the slider, by e.g. the engagement of the plunger of a syringe attached to the sleeve, rotating the hollow mandrel relative to the sleeve will displace the slider and the coiled section of the spring away from the first end of the spring, relative to the hollow mandrel. The displacement maybe equivalent to the length the plunger needed to travel with respect to the syringe barrel, in order to push the fluid out from the syringe.

The slider maybe pushed away from the first end with a distance longer than the plunger travel distance, to reserve in the spring a residual or pre-stressed force for acting on the plunger via the slider. This pre-stressed force is advantageous to provide a relatively more constant force against the plunger until the volume of the fluid filled in the syringe is completely dispensed, to ensure the liquid medicine delivery in a relatively more constant flow rate.

In addition to the practical benefits described above, embodiments described herein provide a technological advantage whereby moving a coiled section of the spring is relatively easier to achieve and control, for example via an axle mechanism coupled to the slider that moves along a track guide in the hollow mandrel.

Another additional advantage is the use of a coupling element on the slider for engaging a syringe plunger in creating a pre-stress force in the spring. The aforesaid coupling element enables the use of the approximate constant range of the force profile in driving the plunger of a syringe, for fluid delivery under a relatively more constant flow rate. The result of achieving a relatively more constant force profile throughout the displaced distance of the plunger enables the syringe to be filled with varying volume of fluid without affecting the intended flow rate of fluid delivery.

A further aspect of the present disclosure is the use of hollow mandrel and telescopic sleeve to support syringes filled with different volume of liquid medicine. In one embodiment, the slider is movably disposed in the hollow mandrel and the syringe is attached to the sleeve. When the hollow mandrel is rotated relative to the sleeve by means of the screw threads engagement, surface overlaps between the sleeve and the hollow mandrel can be progressively adjusted and set at any position relative to each other to adapt to syringes of plungers extended in different lengths. The uncoiling of the coiled section of the spring is due to the action of the plunger and coupling on the slider when the hollow mandrel and the sleeve overlaps incrementally. The combined effect is to displace the coiled section of the spring and the slider away from the first end of the spring which is affixed to the hollow mandrel, causing uncoiling and extension of the spring and storing potential energy in the spring.

In another embodiment, uncoiling of the spring can also be achieved by directly sliding the hollow mandrel into the sleeve element to cause more overlapping surface areas between the sleeve and the hollow mandrel, although the force required in this method is appreciably higher compared to a rotational movement of the sleeve relative to the housing.

BRIEF DESCRIPTION OF THE DRAWINGS

FIG. 2 is an exploded perspective view of FIG. 1A;

FIG. 14 is a diagram showing mobile connectivity of an apparatus of FIG. 1.

DETAILED DESCRIPTION

Figure 1A:
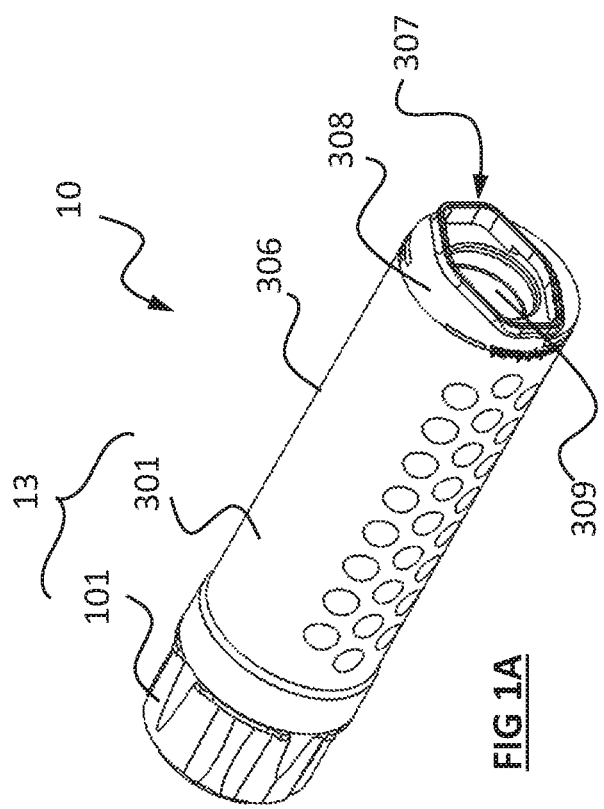
FIG. 1A is a perspective view of an apparatus for delivering fluid according to one embodiment.
Figure 1B:
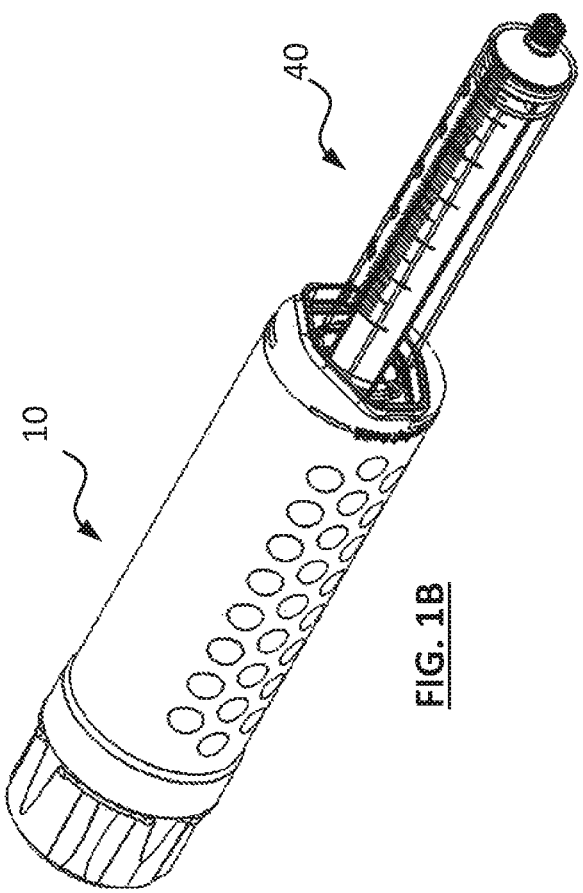
FIG. 1B is a perspective view showing the apparatus of FIG. 1A to which a fluid container is attached for fluid delivery.
Figure 3:
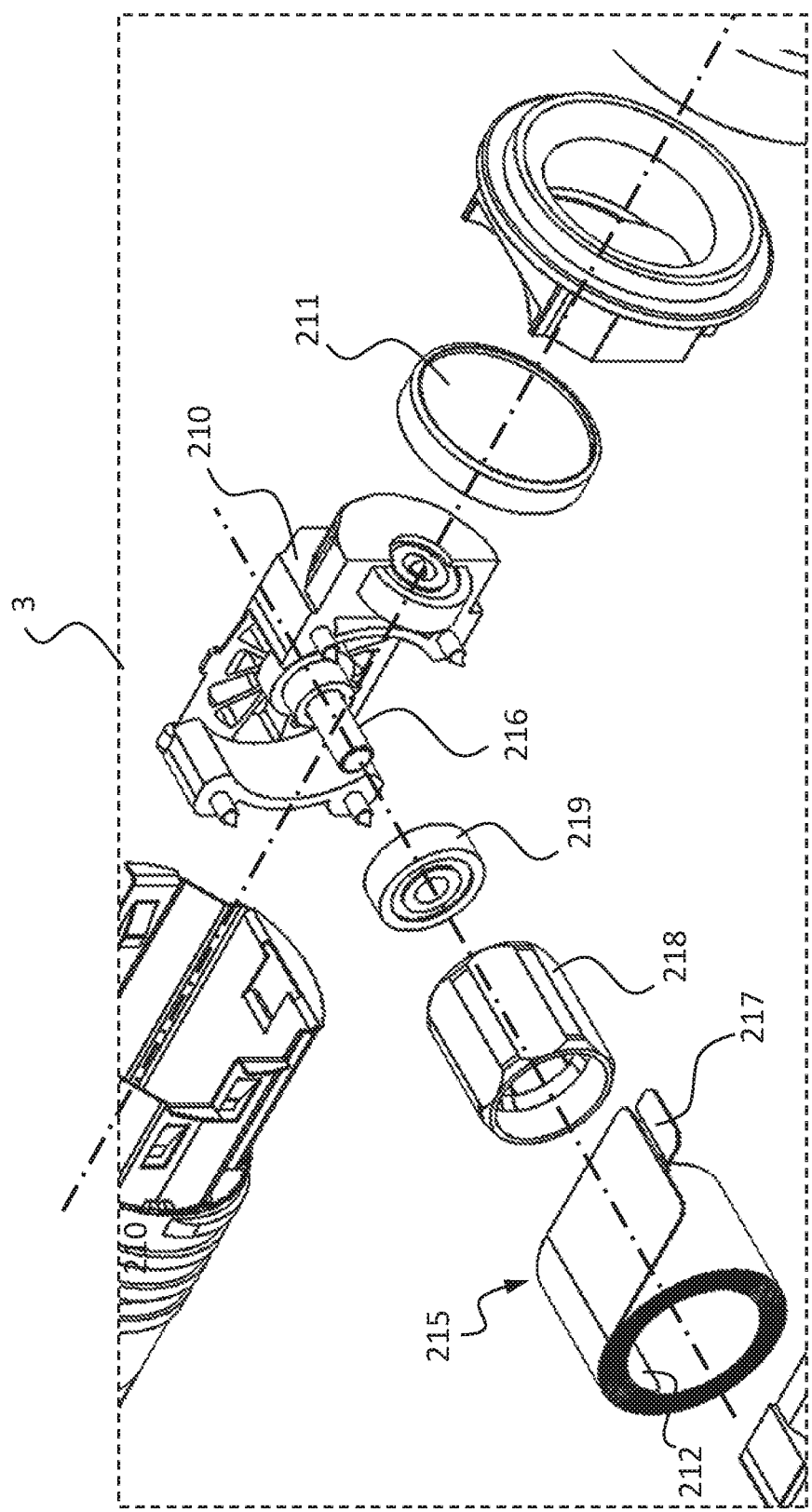
FIG. 3 is a partial enlarged view of portion 3 of FIG. 2.

Examples of embodiments will be shown to provide an understanding of the principles of the design features, its function, manufacture, use of the device and methods disclosed. The embodiments shown are intended to be exemplary and non-limiting. The features described in the embodiment may be combined with variants or modifications of other embodiments to achieve the goals of a device with the features and novelties described. Such variants or modifications are intended to be within the scope of the present disclosure.

By way of a non-limiting example, FIGS. 1A, 1B, 2 and 3 illustrate an apparatus 10 for delivering fluid from a fluid container according to one embodiment. Apparatus 10 has a housing 13, a slider 210 movably disposed in housing 13 and a resilient member 215 connected between the housing 13 and the slider 210. In the present embodiment, housing 13 includes a hollow mandrel 101 and a sleeve 301 movably coupled to hollow mandrel 101, and slider 210 is movably disposed in the hollow mandrel 101. Sleeve 301 has an entrance 307 formed at one end. Entrance 307 includes a rim 308 extending radially and inwardly from side wall 306 of sleeve 301, and an opening 309 surrounded by rim 308.

The resilient member is a thin, flat shaped tape spring 215 made of elastically deformable material, e.g. metal, and coiled to form a reel as shown in FIGS. 2, 3, 4A and 4B. Spring 215 has a first end 217 at the outer end of the reel, and a second end 212 at the inner end of the reel. Spring 215 is wound around an axle 216 at the second end 212, and the axle 216 is attached to the slider 210. A hollow core 218 may be used to support spring 215 and coupled to axle 216 via a bearing 219. The first end 217 extends out of the slider 210 and is connected to the housing 13 i.e. in the present embodiment, the first end 217 is connected to the hollow mandrel 101.

Figure 4:
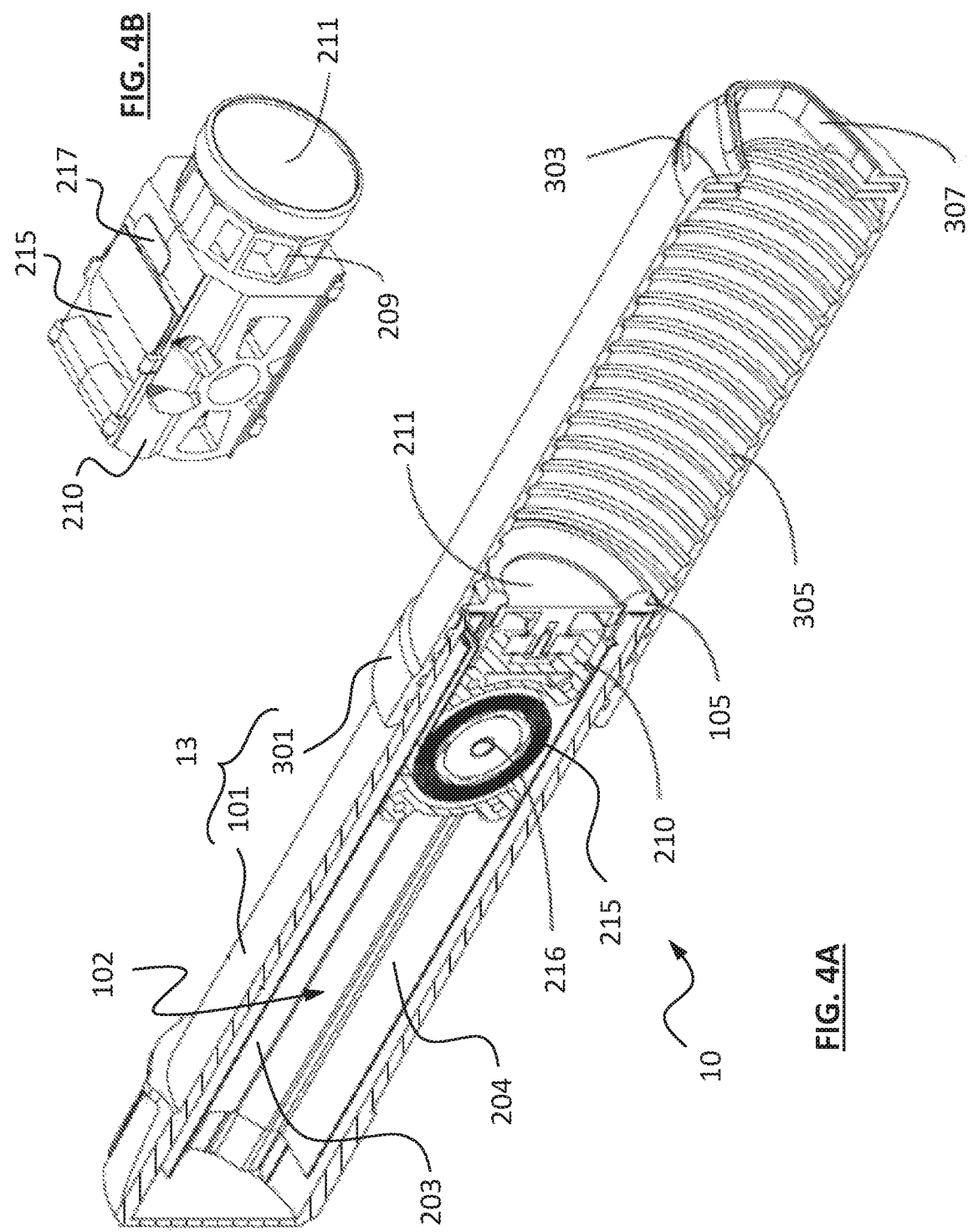
FIG. 4A is a cross sectional perspective view of FIG. 1A showing the slider at the first position adjacent to the entrance of the sleeve.
FIG. 4B is a perspective view showing the position of the slider of the apparatus shown in FIG. 4A.
Figure 5:
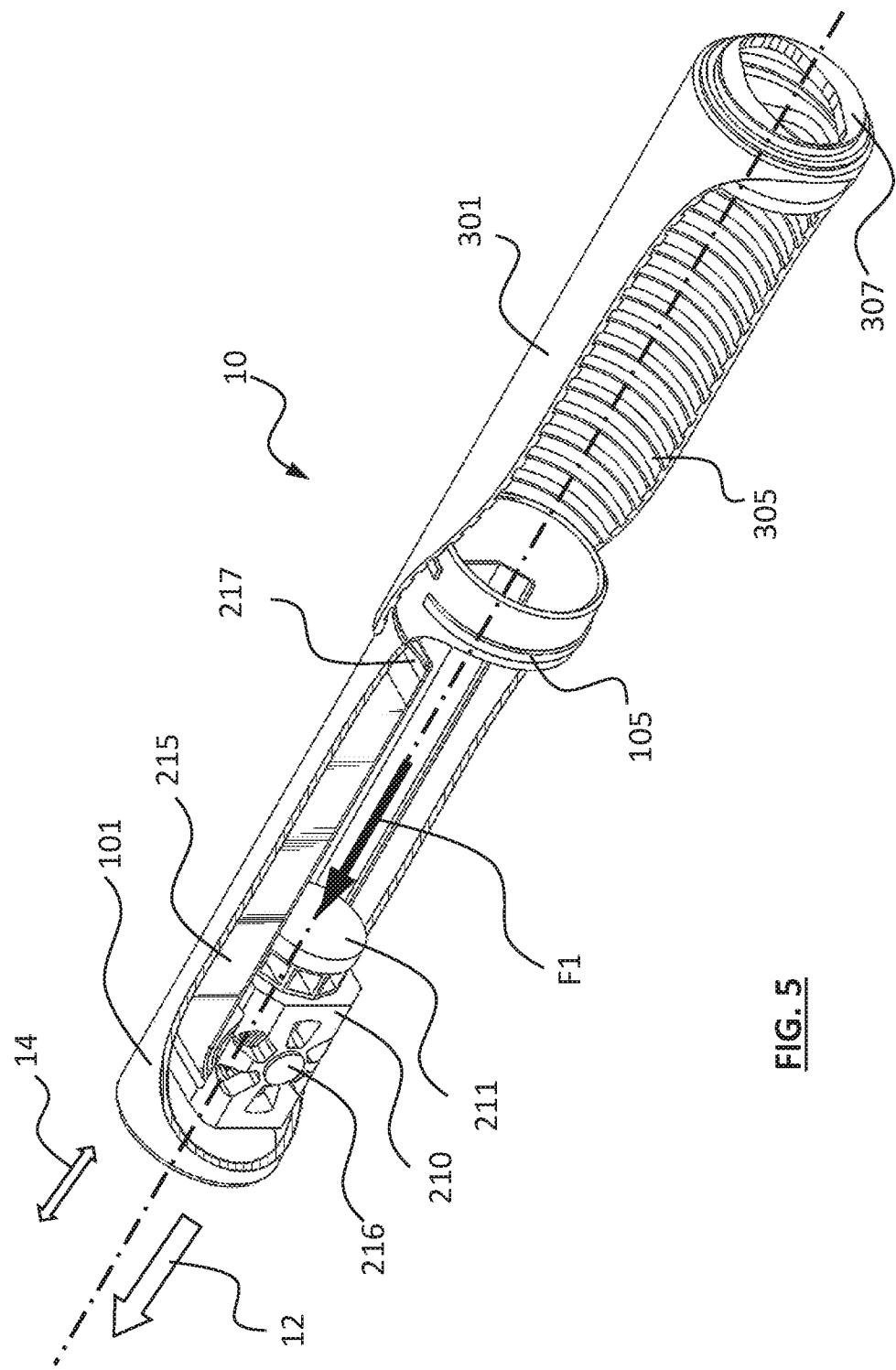
FIG. 5 is a cross sectional perspective view of FIG. 1A showing the slider at the second position.

The spring 215 is at the original, un-deformed state when coiled and with a major portion of the spring 215 received in the slider 210, as shown in FIGS. 4A and 4B. Upon receiving an external force F1, the slider 210 moves relative to the hollow mandrel 101 away from the entrance 307, causing the spring 215 to be pulled out and uncoil from the slider 210 and stores a potential energy in the spring 215, as shown in FIG. 5. The potential energy will generate a driving force required to push fluid out of a fluid container, such as a syringe, attached to the apparatus 10. The displacement of the slider 210 in the hollow mandrel 101 is constrained by guide channels 203 and 204 that could be made from separately formed parts installed within the inner walls of the hollow mandrel 101, or the guide channels 203 and 204 could be integrated to the hollow mandrel 101 itself. The guide channels 203, 204 assist in aligning the direction of the displacement of the slider 210 to be in a generally parallel direction as the axis of the plunger movement within the fluid container. The choice of the number of springs or its dimensions i.e. width, outer diameter, thickness and spring material determines the force that is desired.

The axle 216 may be configured to be free to rotate relative to the slider 210, to ease the spring 215 coiling and uncoiling about the axle 216. Alternatively, axle 216 may be fixed to slider 210 while the second end 212 of the spring 215 is rotatably attached around the axle 216 to maintain connection between the slider 210 and the spring 215 during coiling and uncoiling of the spring 215 around the axle 216.

In this embodiment, the constraints in the volume space of the hollow mandrel 101 corresponds to the use of a single spring, in order to provide a desired force for expelling fluid from a fluid container attached to the apparatus 10. In other embodiments, the spring set could be a single spring or multiple springs arranged in appropriate configurations to provide desired force. By way of example, multiple springs could be arranged within a common axis or with their axes along the lateral direction in which they are displaced when the apparatus is in use.

The mandrel 101 shown in FIGS. 4A and 4B is at fully extended position out of the sleeve 301. The slider 210 is disposed in mandrel 101 and movable relative to mandrel 101 long the channels 203 and 204. When the spring 215 is coiled, a majority portion of spring 215 is wound around axle 216 and received in the slider 210, while the slider 210 is located generally at the first position, adjacent to the entrance/open end 307/309 of the sleeve 301 as shown in FIG. 4A. When an external force F1 is applied to slider 210 along direction 12 i.e. away from entrance 307, the slider 210 will be pushed away from entrance 307, as shown in FIG. 5.

The sleeve 301 has helical thread grooves 305 formed on its inner sidewall. Screw threads 105 of corresponding dimension and pitch are formed on the outer surface of the hollow mandrel 101. Engagement of the thread grooves 305 and screw threads 105 will allow rotation of the hollow mandrel 101 relative to the telescopic sleeve 301 and by such rotation, the hollow mandrel 101 will be moved relative to the sleeve 301 along axial direction 14. The screw threads 105 could be a single loop or multiple loops around the outer circumference of the hollow mandrel 101.

As shown in FIGS. 6 and 7(A) to 7(D), in use, a syringe 40 is firstly filled with a desired amount of liquid medicine 401 in the barrel 406. A tubing 415 connected to the nozzle 408 is then shut off, by a valve or clip 417 attached on tubing 415 to seal the liquid medicine 401 in the syringe 40. As such, the plunger 402 is prevented from moving relative to barrel 406.

In this embodiment, a seat 211 is attached to the slider 210, and is rotatable relative to slider 210. The advantages of seat 211 is to reduce torsional forces acting on the plunger 402 by the slider 210, when the mandrel 101 is rotated into the telescopic sleeve 301. However, the slider 210 may also be directly engaged to the plunger, without the presence of seat 211.

Figure 6:
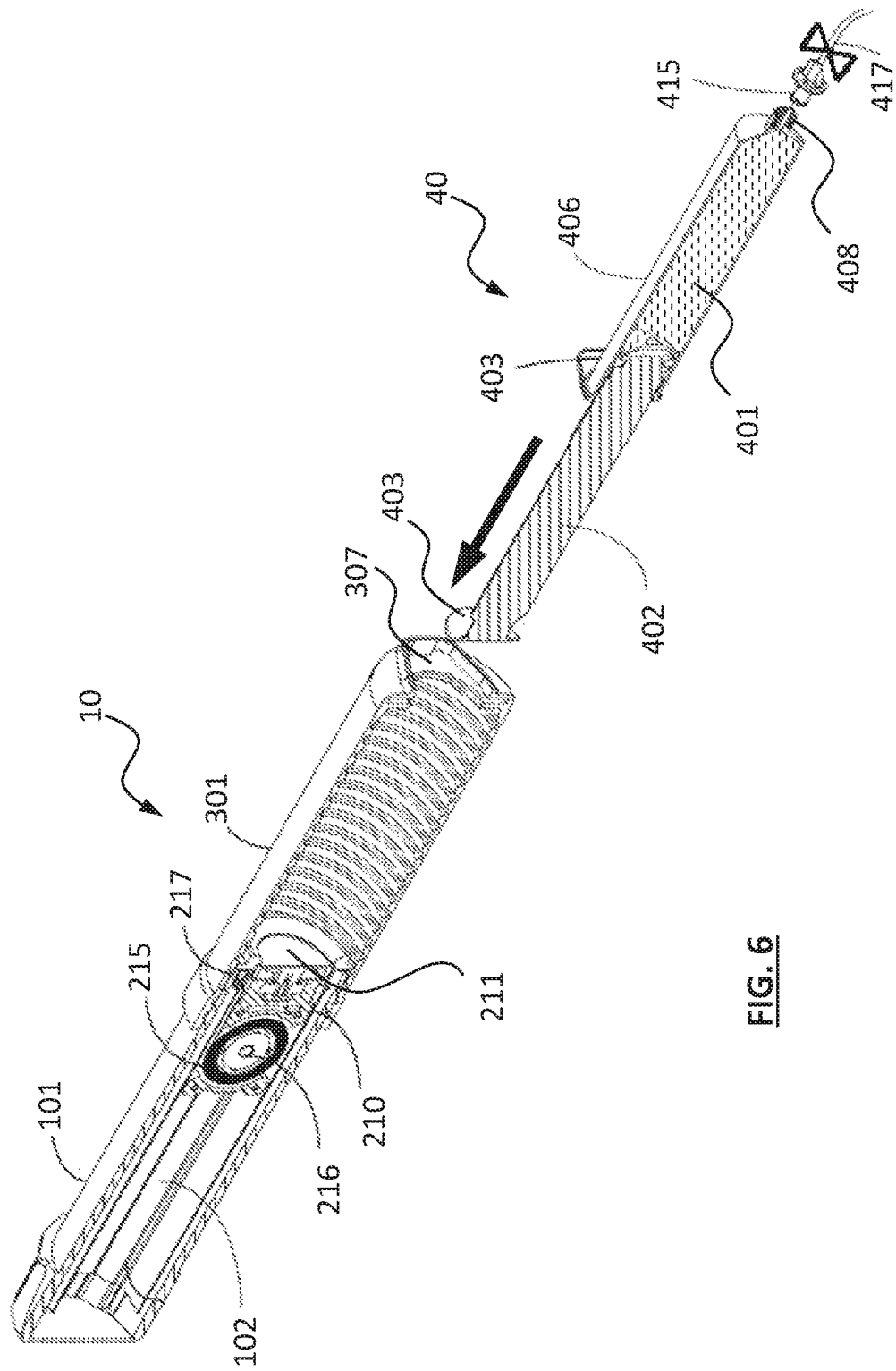
FIG. 6 is a cross sectional perspective view of the apparatus of FIG. 1A to which a filled fluid container is to be attached.
Figure 7:
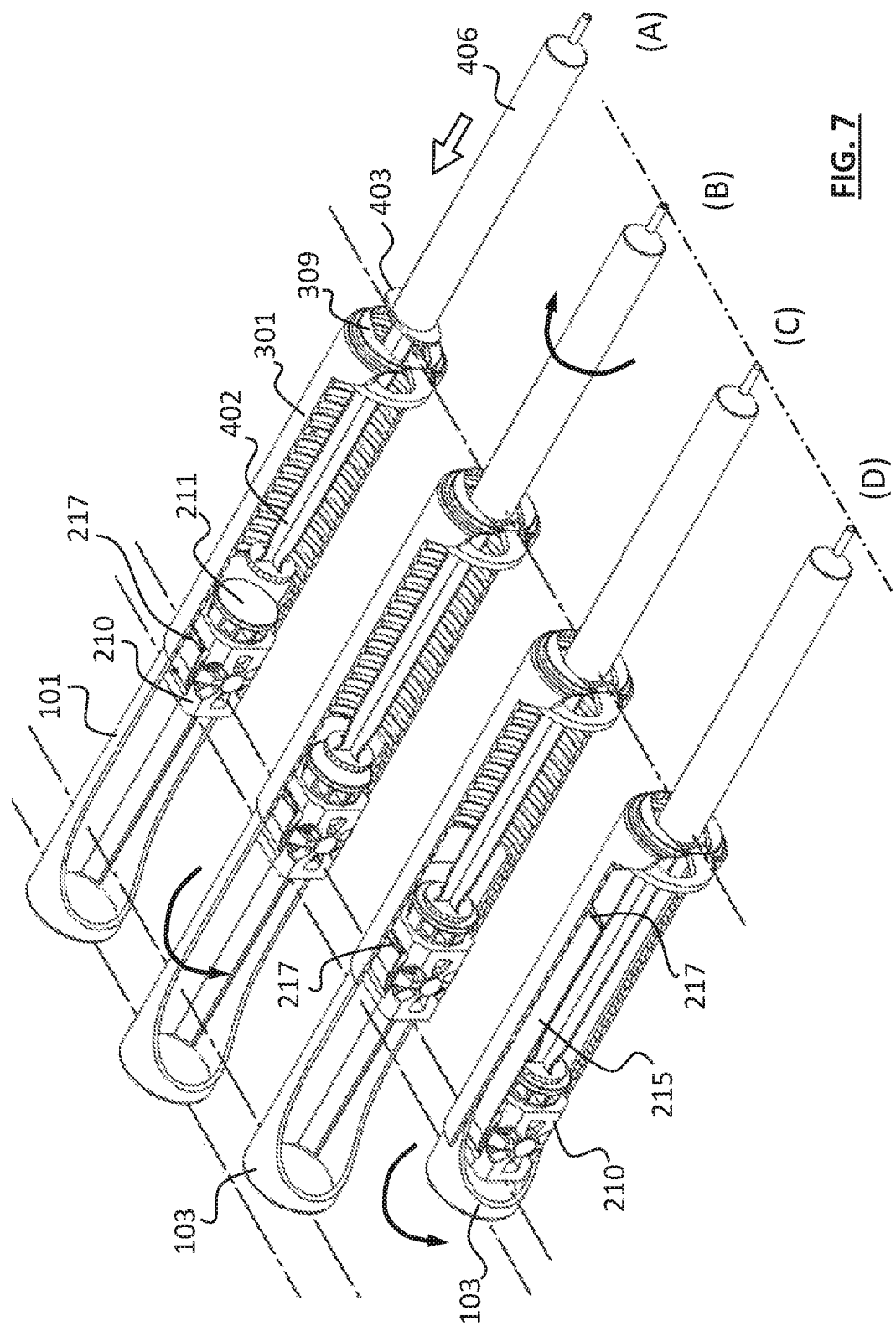
FIGS. 7(A), 7(B), 7(C) and 7(D) are cross sectional perspective views showing a method of attaching a fluid container to the apparatus of FIG. 1.

The plunger 402 is then inserted through entrance 307 of sleeve 301, into hollow mandrel 101 (FIGS. 6 and 7(A)). After the plunger 402 and flange 403 pass through the entrance 307, the barrel 406 of syringe 40 is twisted, by 90 degree for example, so that the oval-shaped flange 403 and similarly oval-shaped opening 309 are positioned with the longer axis of the flange 403 and the longer axis of the opening 309 aligned perpendicular to each other, to lock the barrel 406 to the sleeve 301. Other forms and means of affixing the syringe of other configurations may be adopted which should not be considered to be excluded from the scope as defined by the claims appended thereafter.

Once the barrel 406 is fixed to the sleeve 301, as shown in FIGS. 7(B), 7(C) and 7(D), the mandrel 101 is rotated to move into the sleeve 301, to bring the seat 211 of slider 210 into engagement with the plunger 402. As the barrel 406 and plunger 402 are both relatively stationary with respect to the sleeve 301 since the valve or clip 417 is closed, further advancement of the mandrel 101 into the sleeve 301 will cause the slider 210 to move towards the closed end 103 of the mandrel 101, resulting in the spring 215 being uncoiled and pulled out of the slider 210, as shown in FIG. 7(D).

Figure 8:
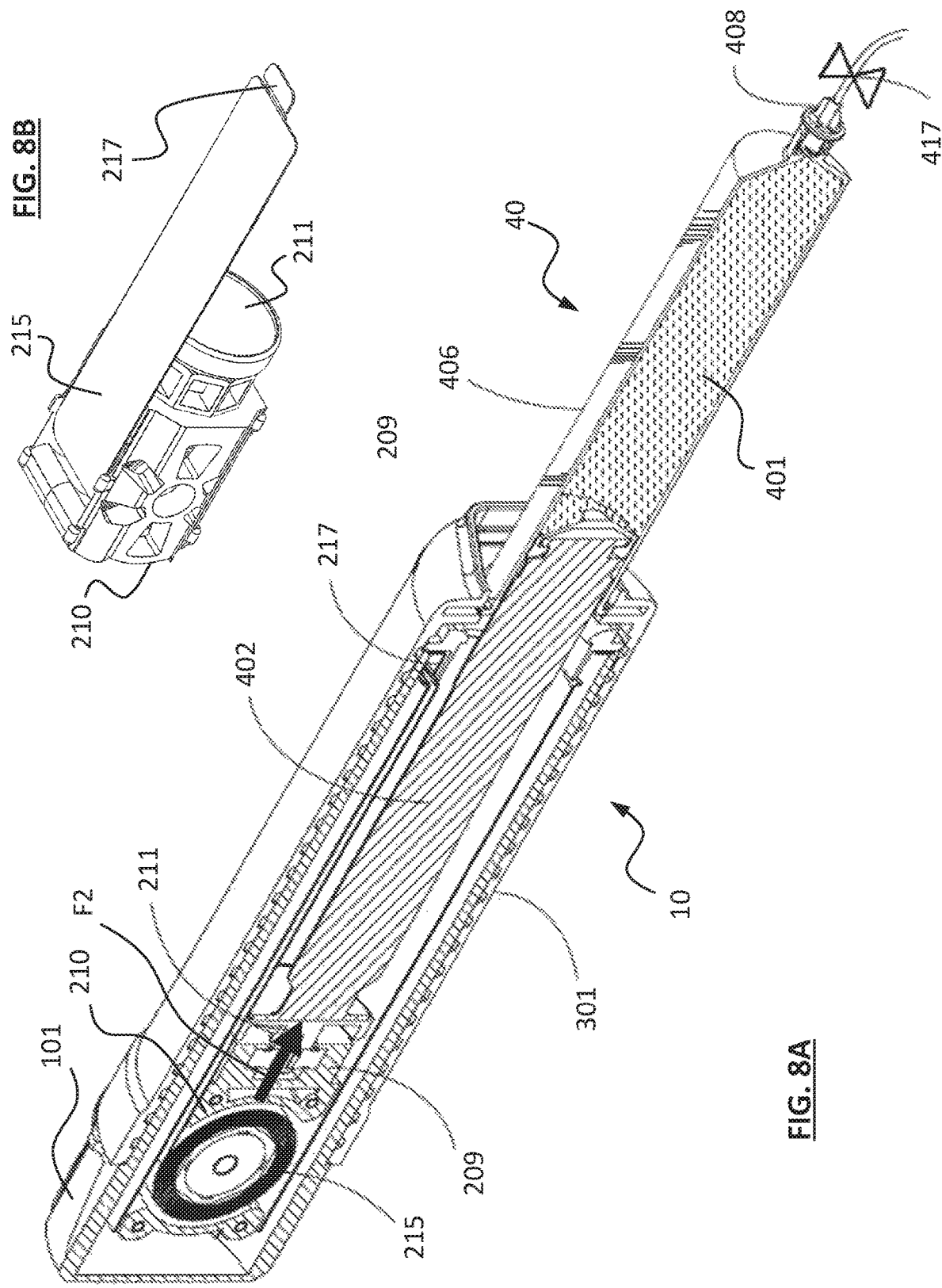
FIG. 8A is a cross sectional perspective view of the apparatus of FIG. 1A to which a fluid container is attached and ready for delivering fluid from the fluid container.
FIG. 8B is a perspective view showing the slider of the apparatus shown in FIG. 8A.
Figure 9:
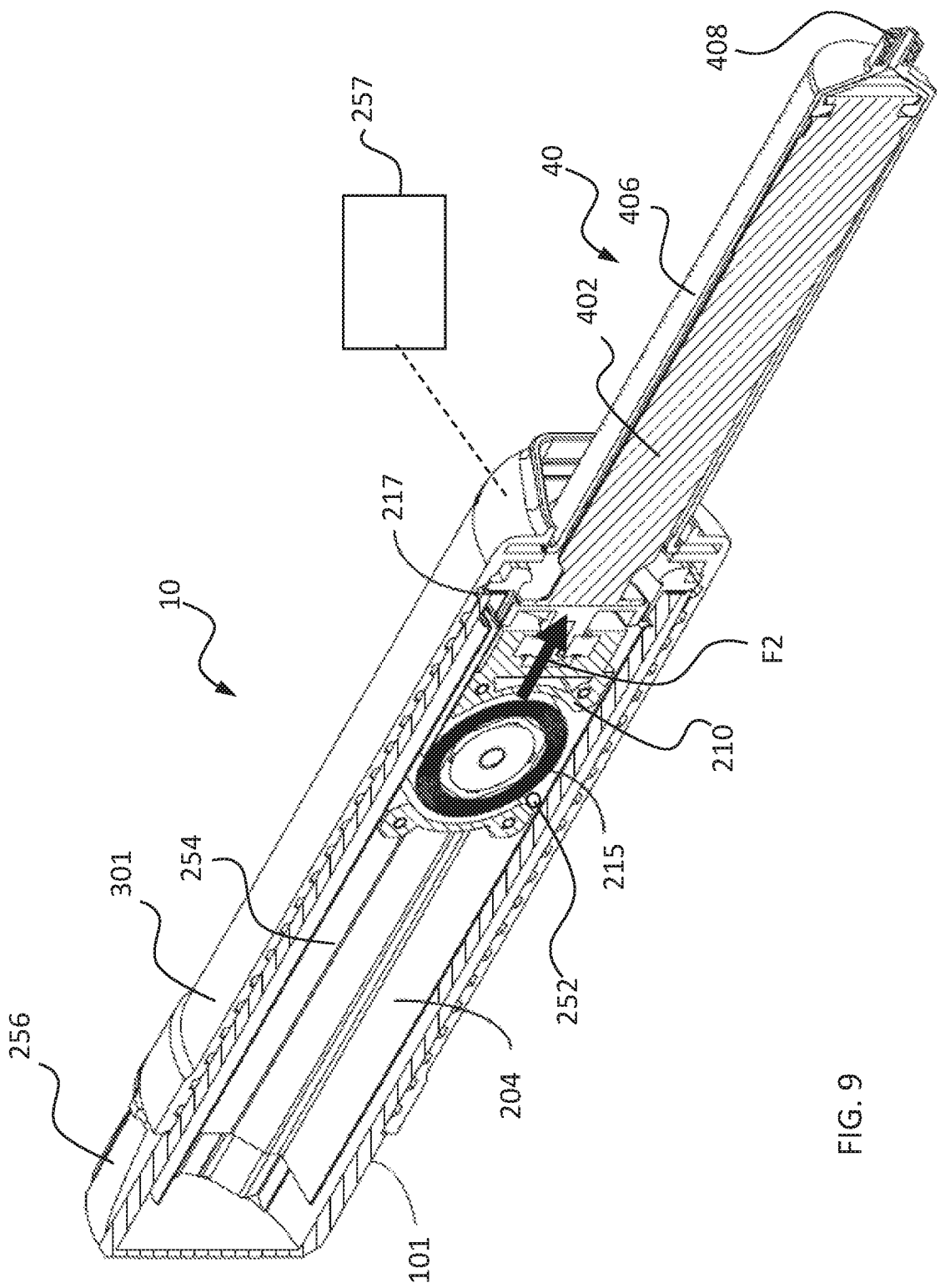
FIG. 9 is a cross sectional perspective view of the apparatus of FIG. 1A to which a fluid container is attached, after completion of the fluid delivery.

With the spring 215 uncoiled, there stores a potential energy in the spring 215 which generates a driving force F2 acting against the plunger 402, as shown in FIG. 8A. The apparatus 10 is now ready for delivering the fluid i.e. liquid medicine from the syringe 40 attached to the apparatus 10. A shown in FIG. 9, when the valve or clip 417 is opened, driving force F2 will prevail, which pushes the plunger 402 to move into the barrel 406 of syringe 40, to expel the liquid medicine 401 out of the syringe 40 through nozzle 408, to complete the fluid delivery. Throughout the whole process of fluid delivery, the driving force F2 is maintained at a substantial constant value, which enables the fluid to be delivered under a contact flow rate.

The slider 210 could be affixed with a magnetic sensor 252 that is in communication with a magnetic linear strip 254 attached on the adjacent channel 203 and/or 204 of housing 13. Interaction of the sensor 252 and strip 254 could detect the position of the slider 210 relative to the mandrel 101, which may be displayed on a screen 256 integrated on the apparatus 10 or onto a separate display 257 in signal communication with the sensor 252.

Figure 11:
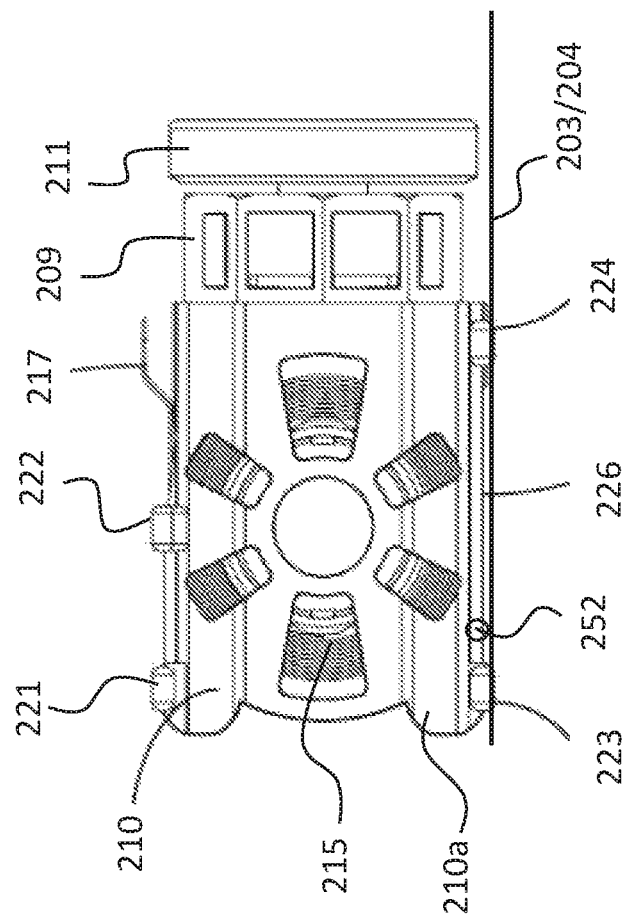
FIG. 11 is a side view of FIG. 10.
Figure 10:
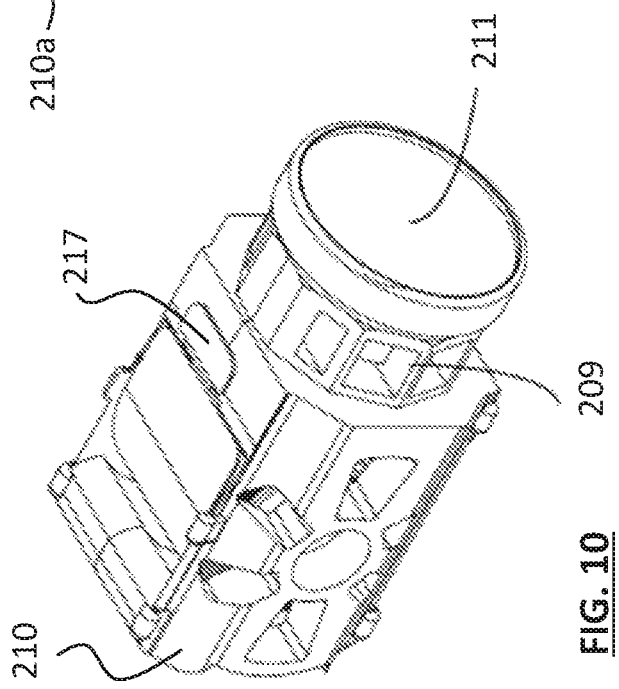
FIG. 10 is a perspective view of the slider and spring assembly of the apparatus shown in FIG. 2.

A shown in FIGS. 10 and 11, projections or stubs 221, 222, 223 and 224 may be formed at the corners of the slider 210 to create a clearance or gap 226 between the main body portion 210a of the slider 210 and the channels 203, 204 that allows displacement sensors 252 to be installed. The communication between the displacement sensor 252 and the display screen 256 or 257 can be established by Bluetooth, WiFi or direct cable connections. A skilled person in the art should be able to extrapolate the data on position and or displacement of the slider 210 relative to the channel 203/204 to obtain valuable information like flow rate at which the fluid is expelled, volume expelled and volume remaining in the syringe. With a built in data base of drug dose limits, commonly known as drug library, the aforesaid data could be used to provide alarms for patient risk situations related to overdose or under dose.

Figure 13:
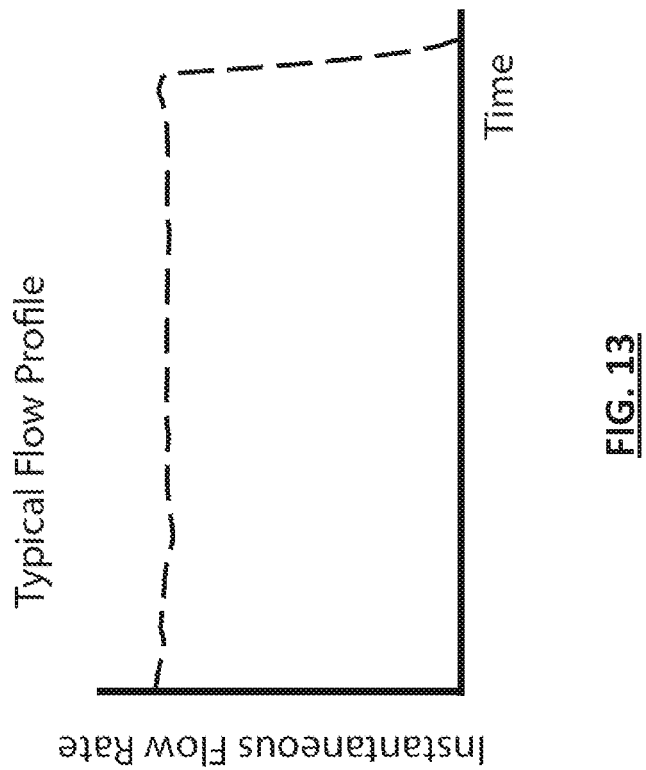
FIG. 13 is a chart showing a flow profile of an apparatus of FIG. 1A used to deliver fluid from a fluid container attached to the apparatus.

Apparatus 10 may include a coupling element 209 positioned and connected between the slider 210 and the seat 211. Coupling element 209 is configured to cause the first end 217 of spring 215 to be positioned at a distance away from the initial unstressed position of the spring 215 within the hollow mandrel 101, such that the total distance the axis of the springs traveled is longer than the displacement required for the plunger 402 to fully discharge the fluid from the syringe. In principle, the length of the coupling element 209 is configured to be sufficient to cause the spring 215 to be uncoiled from the slider 210 so that the driving force F2 exerted on the plunger 402 would have already reached its constant level when fluid start to flow. Typically this deflected length is about 1 to 1.5 times of the outer diameter of the spring 215 in coiled form. The coupling element 209 assists in generating a relatively more constant driving force acting on the fluid through the plunger, resulting in a relatively more constant flow profile during the fluid delivery, as shown in FIG. 13.

Figure 12:
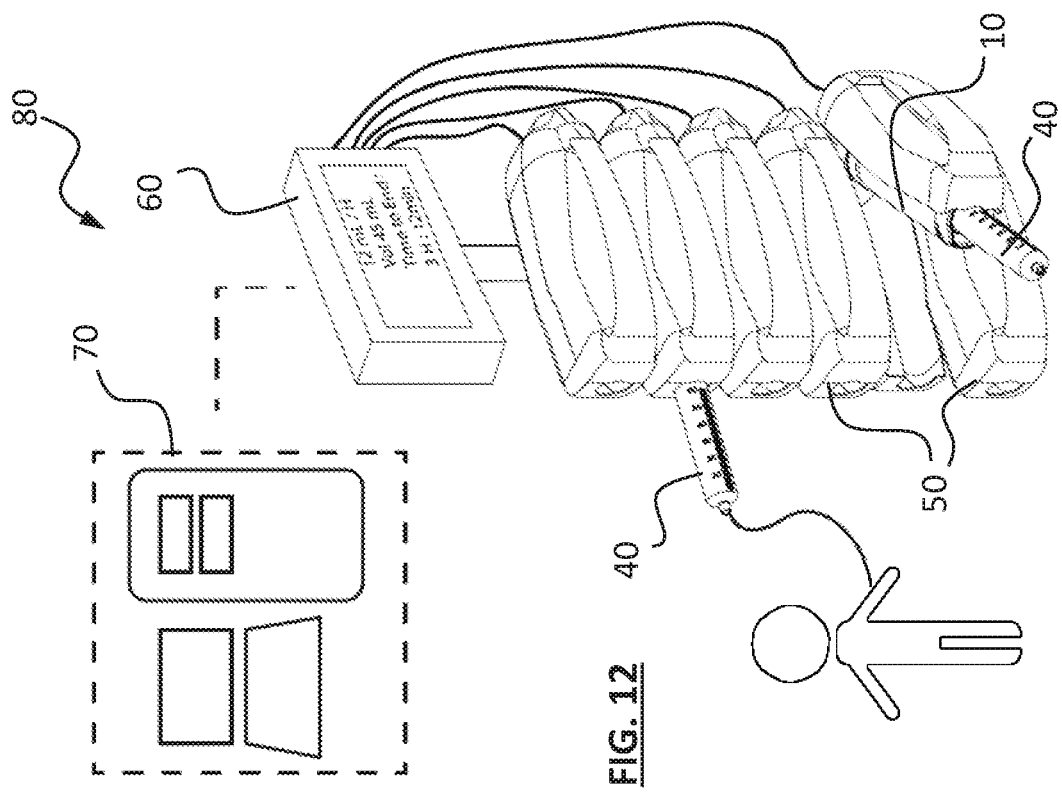
FIG. 12 is a diagram showing a system for fluid delivery according to an embodiment.

FIG. 12 shows a system 80 for fluid delivery. The system 80 includes an array of docking stations 50 each being connected to a display unit 60 that is connected to a controller 70 via a direct or wireless communication network and power supply cable, for use in e.g. a patient centre for automated medication service. Each docking station 50 is configured to detachably hold an apparatus 10 and a syringe 40 attached to the apparatus 10 in a manner as illustrated above. In use, system 80 may be set up at a medical center or any suitable location for providing medication administration to patients.

As shown in FIG. 14, a system 82 for fluid delivery includes one or more apparatus 10 as illustrated above, and a mobile platform 822 connected to each of the apparatus 10 with sensors and stripes installed thereon. Displacement of the slider in each apparatus and flow rate data can be communicated to the mobile platform via wireless network protocols such as Bluetooth, WiFi and/or GSM, which are monitored and controlled for to increase the applicability of the apparatus for medicament delivery to patients.

The invention claimed is:

1. An apparatus comprising:
a housing;
a slider movably disposed in the housing;
a resilient member having a first end connected to the housing and a second end connected to the slider;
a seat member rotatably attached to the slider, and
an extension coupling positioned between the slider and the seat member,
wherein upon receiving an external force, the slider moves relative to the housing to deform the resilient member from a coiled state toward an uncoiled state, and upon release of the external force, the resilient member is allowed to resume to the coiled state for urging the slider against a fluid container attached to the housing to deliver fluid from the fluid container,
wherein the seat member is to abut against the fluid container after the fluid container is attached to the housing, and
wherein the extension coupling is to create a preload on the resilient member when the slider is at a first position.

2. The apparatus as recited in claim 1, wherein the housing includes a mandrel and a sleeve movably coupled to an external surface of the mandrel, the first end of the resilient member is connected to the mandrel and the slider is movably disposed in the mandrel.

3. The apparatus as recited in claim 2, wherein the sleeve is threadedly coupled to the mandrel such that rotation of the mandrel relative to the sleeve about a longitudinal axis moves the mandrel along the longitudinal axis relative to the sleeve.

4. The apparatus as recited in claim 3, wherein upon a fluid container being attached to the sleeve, the fluid container abuts against the slider to move the slider relative to the mandrel during movement of the mandrel into the sleeve.

5. The apparatus as recited in claim 2, wherein the sleeve has an entrance formed at one end thereof, wherein the entrance is to allow a fluid container to be placed therethrough to attach the fluid container to the sleeve.

6. The apparatus as recited in claim 5, wherein upon receiving the external force, the slider moves relative to the mandrel from the first position adjacent to the entrance toward a second position away from the entrance to elastically deform the resilient member from the coiled state to the uncoiled state, and upon release of the external force, the resilient member is allowed to resume to the coiled state to move the slider toward the first position for urging the slider against the fluid container to deliver fluid from the fluid container.

7. The apparatus as recited in claim 1, further comprising a magnetic sensor attached to the slider and a magnetic strip attached to the housing, wherein the sensor and the magnetic linear strip are to detect a positional relationship between the slider and the housing.

8. The apparatus as recited in claim 7, further comprising a screen coupled to the sensor for displaying information related to the positional relationship.

9. The apparatus as recited in claim 8, wherein the slider further comprising one or more stubs projecting from a body portion thereof to form a clearance between the body portion and the housing, wherein the sensor is positioned in the clearance.

10. An apparatus for delivering fluid, the apparatus comprising:
a sleeve to which a fluid container is attachable;
a mandrel movably coupled to and positioned in the sleeve;
a slider movably disposed in the mandrel;
a resilient member connecting the slider to the mandrel;
a seat member rotatably attached to the slider, wherein the seat member is to abut against the fluid container after the fluid container is attached to the sleeve; and
an extension coupling positioned between the slider and the seat member,
wherein upon receiving an external force, the slider moves from a first position toward a second position to uncoil the resilient member, and upon release of the external force, the resilient member is allowed to coil to urge the slider against the fluid container to deliver fluid from the fluid container, and
wherein the extension coupling is to create a preload on the resilient member when the slider is at the first position.

11. The apparatus as recited in claim 10, wherein the sleeve is threadedly coupled to the mandrel such that rotation of the mandrel relative to the sleeve about a longitudinal axis moves the mandrel along the longitudinal axis relative to the sleeve.

12. The apparatus as recited in claim 11, wherein upon the fluid container being attached to the sleeve, the fluid container abuts against the slider to move the slider relative to the mandrel during movement of the mandrel into the sleeve.

13. The apparatus as recited in claim 10, wherein the sleeve has an opening formed at one end thereof, wherein the opening is to allow the fluid container to be placed therethrough to attach the fluid container to the sleeve.

14. A system for delivering fluid, the system comprising:
a syringe having a barrel, a plunger movably coupled to the barrel and a nozzle in fluid communication with the barrel;
an apparatus attached to the syringe, the apparatus comprising:
a housing to which the barrel is attached;
a slider movably disposed in the housing;
a seat member rotatably attached to the slider and abuts against the plunger;
an extension coupling positioned between the slider and the seat member; and
a resilient member having a first end connected to the housing and a second end connected to the slider,
wherein upon the nozzle being closed, the resilient member is elastically deformed from an original state, and upon the nozzle being opened, the resilient member is allowed to resume to the original state to urge the slider against the plunger to deliver fluid from the syringe,
wherein the extension coupling is to create a preload on the resilient member when the resilient member is elastically deformed from the original state.

15. The system as recited in claim 14, further comprising a docking station to which the apparatus is detachably supported.

16. The system as recited in claim 15, further comprising a controller coupled to the docking station and the apparatus, and a screen coupled to the controller for displaying status of the system during fluid delivery.

\* \* \* \* \*